United States Patent
Wittens

(10) Patent No.: US 10,993,820 B2
(45) Date of Patent: May 4, 2021

(54) STENT FOR IMPLANT WITHIN A VEIN

(71) Applicants: Academisch Ziekenhuis Maastricht, Maastricht (NL); Universiteit Maastricht, Maastricht (NL)

(72) Inventor: Cornelis Hendrikus Anna Wittens, Maastricht (NL)

(73) Assignees: Universiteit Maastricht, Maastricht (NL); Academisch Ziekenhuis Maastricht, Maastricht (NL)

(*) Notice: Subject to any disclaimer, the term of this patent is extended or adjusted under 35 U.S.C. 154(b) by 51 days.

(21) Appl. No.: 16/475,276

(22) PCT Filed: Dec. 20, 2017

(86) PCT No.: PCT/NL2017/050857
§ 371 (c)(1),
(2) Date: Jul. 1, 2019

(87) PCT Pub. No.: WO2018/124877
PCT Pub. Date: Jul. 5, 2018

(65) Prior Publication Data
US 2019/0328555 A1 Oct. 31, 2019

(30) Foreign Application Priority Data

Dec. 30, 2016 (EP) .................................... 16207593

(51) Int. Cl.
*A61F 2/82* (2013.01)
*A61F 2/915* (2013.01)

(52) U.S. Cl.
CPC .......... *A61F 2/82* (2013.01); *A61F 2002/825* (2013.01); *A61F 2002/826* (2013.01); *A61F 2002/828* (2013.01); *A61F 2002/91583* (2013.01); *A61F 2250/0007* (2013.01); *A61F 2250/0008* (2013.01)

(58) Field of Classification Search
CPC .......... A61F 2002/825; A61F 2002/826; A61F 2002/828; A61F 2002/91583; A61F 2250/0007; A61F 2250/0008
See application file for complete search history.

(56) References Cited

U.S. PATENT DOCUMENTS

2008/0183275 A1   7/2008  Schmid et al.

FOREIGN PATENT DOCUMENTS

| EP | 2 710 984 A1 | 3/2014 |
| WO | 2013/078497 A1 | 6/2013 |

OTHER PUBLICATIONS

International Search Report for International Application No. PCT/NL2017/050857 dated Feb. 28, 2018.

*Primary Examiner* — David H Willse
*Assistant Examiner* — Javier G Blanco
(74) *Attorney, Agent, or Firm* — Suiter Swantz pc llo

(57) ABSTRACT

The invention relates to stents, in particular to a stent for insertion in a vein of a human or animal body. The invention also relates to a catheter stent insertion device for inserting a stent according to the invention in a vein of a human or animal body. The invention also relates to a method for inserting a stent according to the invention in a vein of a human or animal body using a catheter stent insertion device according to the invention.

8 Claims, 6 Drawing Sheets

STENT FOR IMPLANT WITHIN A VEIN

FIELD OF THE INVENTION

The invention relates to stents, in particular to a stent for insertion in a vein of a human or animal body.

The invention also relates to a catheter stent insertion device for inserting a stent according to the invention in a vein of a human or animal body.

The invention also relates to a method for inserting a stent according to the invention in a vein of a human or animal body using a catheter stent insertion device according to the invention.

BACKGROUND OF THE INVENTION

Stents are widely used in medicine to keep the passageway open of the lumen of an anatomic vessel or duct. There is a wide variety of stents used for different purposes, from expandable coronary, vascular and biliary stents, to simple plastic stents used to allow the flow of urine between kidney and bladder.

In particular, vascular stents are commonly placed in arteries and veins in order to support the affected, weakened vessel wall of the artery or vein, as part of angioplasty. The commonly used procedure of treatment implements a catheter to insert and guide an expandable stent towards the site of the weakened vessel wall. The catheter containing the compressed peripheral stent is hereto inserted into the femoral artery or vein and guided using suitable imaging techniques, such as fluoroscopy, towards the site of deployment. Once the catheter is properly positioned the compressed stent is deployed and expanded against the inner vessel wall of the artery or vein.

Because of the external compression and mechanical forces subjected to these locations, flexible stent materials such as nitinol are used in a majority of peripheral stent placements.

Segmental stents being composed of at least two individual interconnected stent segments with a high radial force and high flexibility can be implemented within veins, due to the low shear stress conditions in the venous system. A problem associated with such stents being assembled of multiple stent segments is that once the most proximal stent segment is being deployed from the catheter stent insertion device at the desired or intended deployment location within the vein, the deployed stent segment immediately will expand into its expanded configuration and come in abutment with the inner vessel wall of the vein.

Any retraction of the deployed and expanded stent segment back into the catheter stent insertion device for repositioning purposes within the vein, for example due to a deployment (and expansion) on an incorrect or non-preferred position within the vein, is no longer possible. The position of an already deployed and expanded first stent segment within the vein cannot be corrected and the remainder of the stent assembly yet accommodated in the catheter stent insertion device has to be deployed entirely within the vein. This may lead to a stent being deployed and expanded, which does not fully support the affected vessel wall of the vein over its intended length and as such the stenting procedure may not be considered successful.

DESCRIPTION OF THE INVENTION

The invention aims to provide a solution for the above identified problem, allowing the correction of the ultimate deployment position of the stent assembly within the vein, such that after correction the affected vessel wall of the vein is properly supported over its full length by the deployed and expanded stent.

According to the invention a stent for insertion in a vein of a human or animal body is proposed, said stent having a proximal end, a distal end and a longitudinal stent axis and comprising at least two stent segments, as well as segment interconnecting means interconnecting two stent segments, wherein said segment interconnecting means are arranged in adjusting a distance between said two stent segments between a first configuration, wherein said distance is minimal and a second configuration, wherein said distance is maximal, due to a rotation around said longitudinal stent axis of one of said two stent segments relative to the other of the two stent segments.

This allows for adjusting the length of the stent with respect of the intended location of deployment within the vein, such that the affected vessel wall of the vein always is properly supported over its full length by the adjusted stent after deployment and expansion in the vein.

In an example of the stent according to the invention, for interconnecting said at least two stent segments, said segment interconnecting means comprise at least one elongated filament rod having two rod ends, a first rod end being connected to the first stent segment and the second rod end being connected to the second stent segment, wherein in said first configuration said first rod end and said second rod end are radially offset with respect to each other and wherein in said second configuration said first rod end and said second rod end are longitudinally aligned with respect to each other.

Thus the stent segments are always properly interconnected, and the coherence or unity of the overall stent assembly is maintained. As a result of the initial orientation of the filament rods in the compressed configuration of the stent a length adjustment of the stent due to rotation of the relevant stent segments relative to each other can be effectively realized.

Furthermore, in yet another example of a stent according to the invention, which is capable of supporting or stenting larger lengths of affected vessel walls of a vein, or even may be implanted in meandering vein parts, the stent comprises a proximal stent segment, a distal stent segment and one or more intermediate stent segments disposed between the proximal and distal stent segments, and wherein said segment interconnecting means interconnect each of said stent segments.

In this example furthermore said proximal stent segment has a first length, said distal stent segment has a second length, and said intermediate stent segments have a third length, all seen along said longitudinal axis of the stent, wherein said third length is smaller than said first and second length, and in particular said third length is 5-15 mm. As such the stent assembly has a proximal stent part as well as a distal stent part of a longer length that the individual intermediate stent segment. The longer stent length at its proximal and distal end part serves as a proper support for the affected vessel wall at the beginning and the end of the expanded stent within the vein. This guarantees a proper and stable anchoring of the stent within the vein.

In this simplified example said first length and said second length are the same, whereas in another example said first length is longer than said second length, in particular said first length is 30-50 mm and said second length is 10-30 mm.

In yet another example said maximal distance between said stent segments is 5-20 mm.

Depending on the stenting procedure to be performed on the affected vein of the patent, the number of said intermediate stent segments is between 1-30.

An example of a catheter stent insertion device for inserting a stent composed of at least two stent segments according to the invention in a vein of a human or animal body is proposed, which catheter stent insertion device allows for adjusting the length of the stent with respect of the intended location of deployment within the vein, such that the affected vessel wall of the vein always is properly supported over its full length by the adjusted stent after deployment and expansion in the vein.

Hereto the catheter stent insertion device according to the invention at least comprises a hollow stent accommodating tube having an open proximal tube end and a distal tube end, said hollow stent accommodating tube being arranged for accommodating said stent in a compressed configuration, as well as guidance means for guiding said hollow stent accommodating tube with its proximal tube end towards a deployment location within said vein, as well as deployment means for advancing said compressed stent along its longitudinal stent axis towards said open proximal tube end and within said vein at said deployment location, such that said stent expands and abuts against the inner vessel wall of the vein, and wherein said deployment means are arranged in adjusting a distance between said at least two stent segments between a first configuration, wherein said distance is minimal and a second configuration, wherein said distance is maximal, by rotating one of said at least two stent segments around the longitudinal stent axis relative to the other of the at least two stent segments.

This allows for adjusting the length of the stent with respect of the intended location of deployment within the vein, such that the affected vessel wall of the vein always is properly supported over its full length by the adjusted stent after deployment and expansion in the vein.

In a further example of the said deployment means are arranged in adjusting said distance between said at least two stent segments within said hollow stent accommodating tube. Thus the stent can be adjusted and preset at its correct length prior to the actual deployment and expansion within the vein.

This allows for last minute adjustments by the physician for example based on real time imaging information of the intended deployment position within the vein.

In particular, said deployment means comprises multiple engagement notches, the number of engagement notches being conformal to the number of stent segments of the stent, and wherein each of said multiple engagement notches are arranged in engaging the respective stent segment in a rotational and longitudinal direction.

In an example of the catheter stent insertion device according to the invention said deployment means comprise a spindle shaft extending through the hollow stent accommodating tube and within the compressed stent, said spindle shaft being provided with said radially outward projecting multiple engagement notches.

In particular, each engagement notch exhibits a contact surface oriented towards the proximal tube end, as well as a contact surface oriented towards the distal tube end, said proximal contact surface exhibiting an acute angle with the longitudinal axis towards the proximal tube end of 90° or less, and said distal contact surface exhibiting an obtuse angle with the longitudinal axis towards the distal tube end.

As such a proper engagement of the notches with the metal mesh material of the several stent segments in a longitudinal proximal direction and rotational direction is realized, whereas the engagement is released and absent upon retraction of the spindle shaft in the longitudinal distal direction.

The invention also relates to a method for inserting a stent according to the invention at a deployment location within a vein of a human or animal body using a catheter stent insertion device according to the invention, the method comprising the steps of:

A inserting the catheter stent insertion device accommodating said stent composed of at least two stent segments in a compressed configuration in said hollow stent accommodating tube with its open proximal tube end in the vein;

B guiding the catheter stent insertion device towards said deployment location within the vein;

C advancing the stent within the hollow stent accommodating tube until the proximal one of the at least two stent segments is in the correct position and deployed via the open proximal tube end in the vein;

D rotating one of said at least two stent segments around the longitudinal stent axis relative to the other of the at least two stent segments, thereby adjusting a distance between said at least two stent segments between a first configuration, wherein said distance is minimal and a second configuration, wherein said distance is maximal;

E advancing the stent within the hollow stent accommodating tube, and deploying the next proximal one of the at least two stent segments via the open proximal tube end in the vein.

In particular the method is further characterized by the step of:

D1 repeating step D for each next proximal individual stent segment of the stent.

In yet another example, in the method steps D and D1 are performed for each of the individual stent segments within the hollow stent accommodating tube prior to step C.

BRIEF DESCRIPTION OF THE DRAWINGS

The invention will now be described in more details in reference to the accompanying drawings, which drawings show in:

FIGS. 5A-5B-50 detail view of the stent of FIGS. 1-4 in several expansion states;

DETAILED DESCRIPTION OF THE INVENTION

Figure 1:
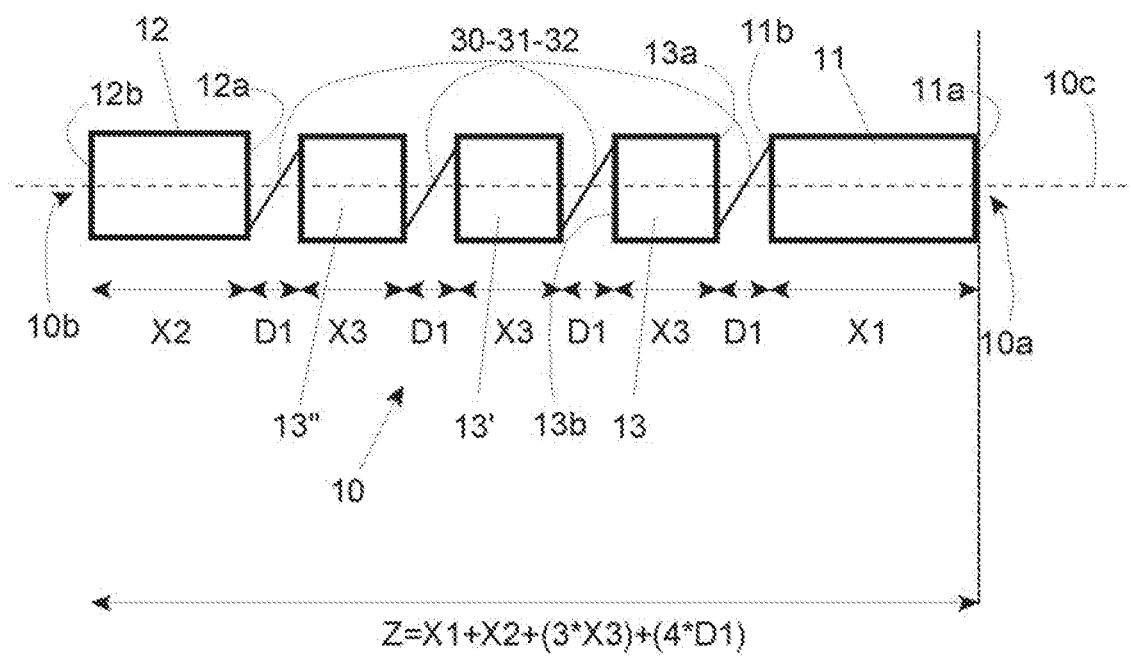
FIG. 1 a schematic example of a stent according to the invention.

For a better understanding of the invention like parts in the drawings are to be denoted with like reference numerals.

In the detailed description below as well as in the claims various parts are denoted with the classification "proximal" and "distal". These classifications are to be considered in relation to the location of the heart of the human or animal subject in which the stent is to be implanted. Hence the classification "proximal" is to be understood as meaning "closest to the heart" or "in a direction towards the heart".

Similarly "distal" is to be understood as meaning "farthest from the heart" or "in a direction away from the heart".

In FIGS. 1, 2, 3 and 4, an example of a stent assembly according to the invention is shown. In FIGS. 1-4 the stent assembly is denoted with reference numeral 10.

Stent assembly 10 comprises a proximal stent segment 11 with a proximal segment face 11a, which corresponds with the proximal stent end 10a of the complete stent assembly 10. The proximal stent segment 11 also has a distal segment face 11b. The stent assembly 10 also comprises a distal stent segment 12, which in a similar fashion is provided with a proximal segment face 12a and a distal segment face 12b, the latter also forming the distal stent end 10b of the stent assembly 10.

Between the proximal stent segment 11 and the distal stent segment 12, several intermediate stent segments 13, 13' and 13" are accommodated. It is to be noted that the number of intermediate stent segments can be arbitrarily chosen. Next to the embodiment as shown in FIGS. 1-4, which depicts three intermediate stent segments 13-13'-13", any arbitrary number of intermediate stent segments 13 (one, two, three, four, . . . till 30 or more) can be chosen, depending on the stent implant application to be performed.

In this example, the intermediate stent segments 13-13'-13"-etc. are identical in terms of shape and dimensions. However this equal configuration is not required for the functionality of the stent 10 according to the invention.

The stent assembly 10 depicted in the FIGS. 1-4 is accommodated in a compressed configuration in a catheter stent insertion device with the individual compressed stent segments 12-13"-13'-13-11 (seen from the distal stent end 10b towards the proximal stent end 10a of the stent 10) all being positioned at a minimal distance D1 (theoretically 0 (zero) mm, but in practice around 0.5-1.0 mm) from each other. The proximal stent end 10a forms the frontal part of the stent assembly 10, seen in relation to the orientation of the heart of the human or animal body.

As the proximal stent segment 11 is to be inserted and deployed as the first segment within the vein of a human or animal body, the initial length X1 of the proximal stent segment 11 needs to be sufficiently long, allowing for a partial, incomplete insertion and deployment of the proximal stent segment 11 into the vein and checking of its correct position within the vein using suitable known imaging techniques, such as fluoroscopy, and a subsequent retraction of said partially deployed proximal stent segment 11 back into the catheter stent insertion device in case of an incorrect position being observed.

Preferably the length X1 is such that a partial deployment of the first, proximal stent segment 11 within the vein over approximately an insertion/deployment length corresponding with 50% of X1 still allows for a proper retraction of said partially deployed proximal stent segment 11 back into the catheter stent insertion device and a subsequent repositioning of the (proximal end of the) catheter stent insertion device within the vein for a renewed, now correct deployment of the proximal stent segment 11.

In this example the individual stent lengths X1 of the proximal stent segment 11) and X2 (being the length of the distal stent segment 12) are both larger than the individual stent length X3 of the intermediate stent segment (either 13-13'-13"). For example X1 and X2 are of an identical length, whereas in the FIGS. 1-4 it is shown that X1 is larger than X2. Typical dimensions for X1, X2 and X3 are: X1 between 30-50 mm, X2 between 10-30 mm and X3 between 5-15 mm. A typical diameter of all stent segments, hence the overall stent assembly 10 is between 10-35 mm.

The stent assembly 10, as depicted in FIG. 1, is shown in its initial configuration within the catheter stent insertion device, meaning that the stent assembly 10 has a minimal length, measured from its proximal stent end 10a until its distal stent end 10b. Said minimal length is denoted with the reference numeral Z. The initial overall length Z of the stent assembly 10 as denoted in FIG. 2 is composed of (the summation of) the individual stent length X1 (of the proximal stent segment 11), X2 (the length of the distal stent segment 12), three times the individual stent length X3 of the three intermediate stent segments 13-13'-13", as well as four times the minimal distance D1 present between each adjacent stent segment.

Figure 2:
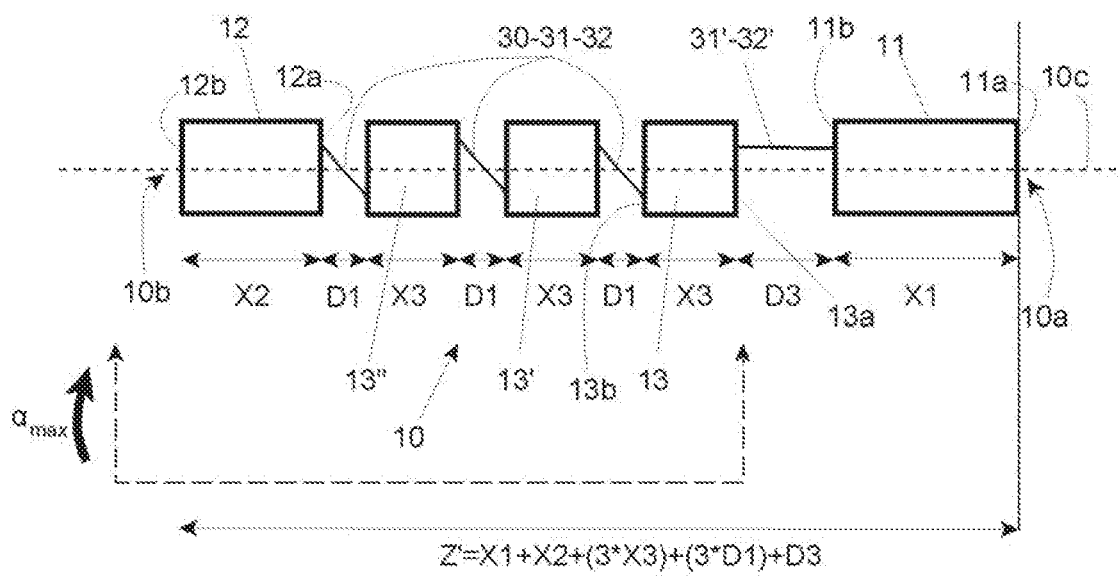
FIG. 2 a schematic example of the stent of FIG. 1 in a first expansion state.

In FIG. 2, the stent assembly 10 of FIG. 1 is depicted in a first intermediate expanded configuration. In a manner similar to the expansion procedure described in more detail in connection with FIGS. 5A-5B-5C, the elongated rod elements 31'-32' which interconnect the proximal stent segment 11 with the first intermediate stent segment 13, have been set in a parallel orientation to the longitudinal axis 10c of the stent assembly 10. As such, the initial minimum distance D1 between the proximal stent segment 11 and the first intermediate stent segment 13 as depicted in FIG. 1, has been adjusted to its maximum distance, now depicted with the reference numeral D3.

Adjusting the distance D1 between the proximal stent segment 11 and the first intermediate stent segment 13 from its initial, minimum distance D1 to its maximum distance D3, is established by simultaneous rotation of the three intermediate stent segments 13-13'-13", together with the distal stent segment 12 around its longitudinal stent axis 10c over its maximum rotation angle $\alpha_{max}$, relative to the proximal first stent segment 11 (which remains static and does not displace). This simultaneous rotation over the rotation angle $\alpha_{max}$ around the longitudinal stent axis 10c is depicted with the dashed two-ended arrow which encompasses the three intermediate stent segments 13-13'-13", as well as the distal stent segment 12. The intermediate overall stent length Z' now corresponds to the summation of the initial stent lengths X1, X2, X3 (triple), as well as three times the minimal distance D1 and a maximum distance D3.

Here it is to be noted that in an example of the deployment technique the first, proximal stent 11 is already inserted and deployed within the vein, with the remainder of the stents 13-13'-13"-12 still accommodated in a compressed state within the catheter stent insertion device and ready for a next length adjustment as described below in relation to FIG. 3.

Figure 3:
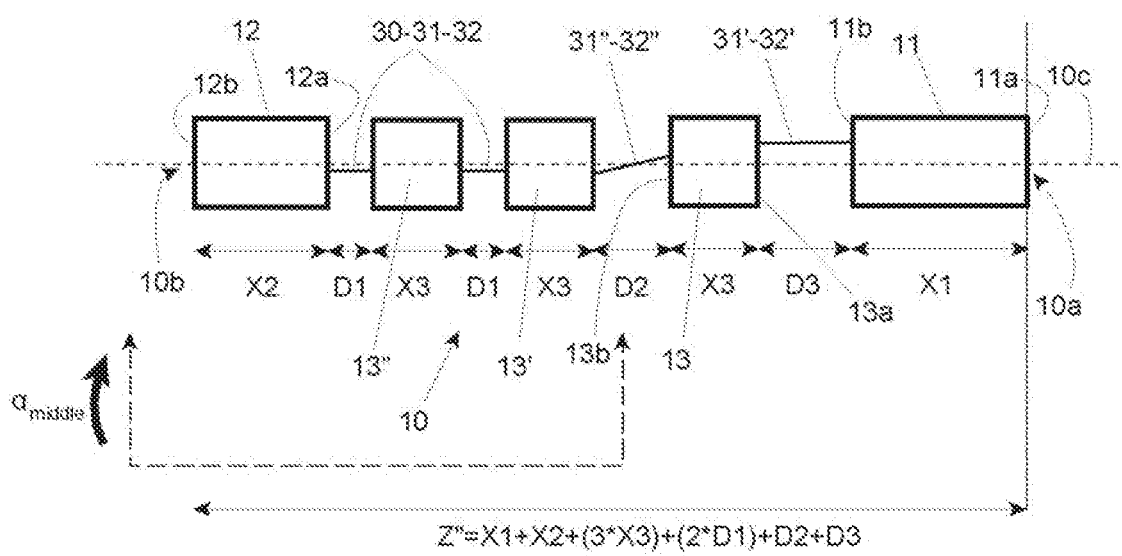
FIG. 3 a schematic example of the stent of FIG. 1 in a further expansion state.

FIG. 3 depicts the stent assembly 10, which, from its starting position shown in FIG. 2, has been extended further by adjusting the initial minimum distance D1 between the intermediate stent segment 13 and the intermediate stent segment 13' (see FIG. 3) to an intermediate distance, now depicted with reference numeral D2 in FIG. 3. The adjustment of the distance between the first intermediate stent segment 13 and the second intermediate stent segment 13' is accomplished by the simultaneous rotation over a rotation angle $\alpha_{middle}$ (approx. 60-90°) around the longitudinal stent axis 10c of the set of the second and third intermediate stent segments 13' and 13", together with the distal stent segment 12 relative to the proximal stent segment 11 and the first intermediate stent segment 13, which remain static and do not displace.

The resulting overall stent length Z" is composed of the individual stent lengths X1, X2, and three times X3, as well as two minimal distances D1, one maximum distance D3 (as being set in the stent configuration shown in FIG. 1) and the intermediate distance D2.

Likewise, the next, proximal stent 13 is also already inserted and deployed within the vein, with the remainder of the stents 13'-13"-12 still accommodated in a compressed state within the catheter stent insertion device and ready for a next length adjustment as described below in relation to FIG. 4.

Figure 4:
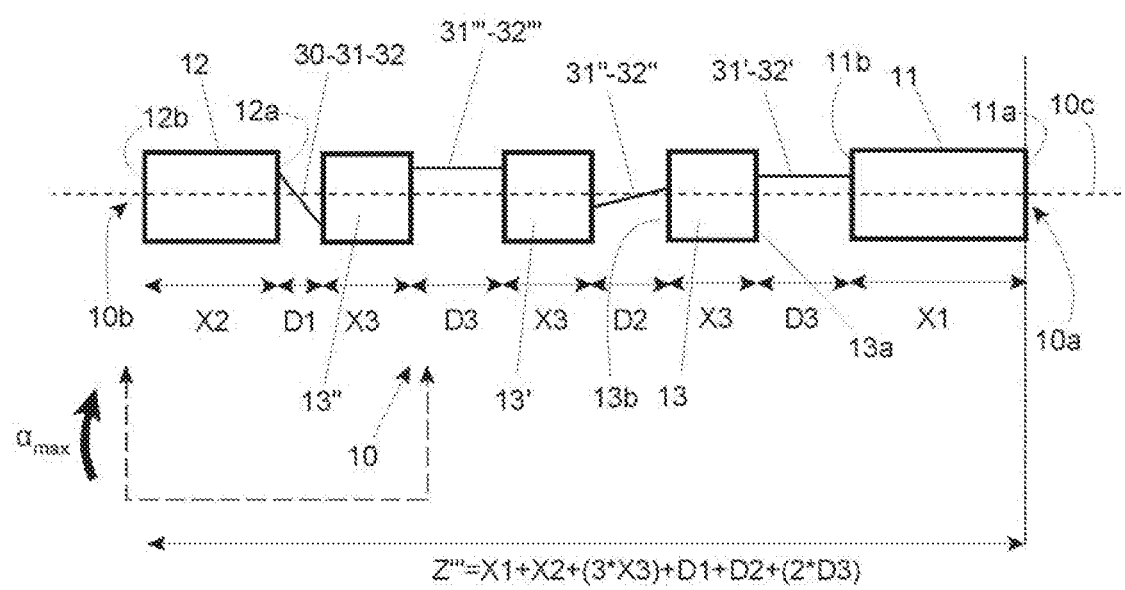
FIG. 4 a schematic example of the stent of FIG. 1 in a yet a further expansion state.

FIG. 4 shows yet another configuration of the stent assembly 10, which now exhibits an overall stent length of Z'". The new stent length Z'" has been created by a further extension step, wherein the third intermediate stent segment 13", together with the distal stent segment 12, is being rotated around the stent axis 10c over its maximum rotation angle $\alpha_{max}$, relative to the proximal stent segment 11, the first and second intermediate stent segments 13-13', which remain static and do not displace.

In an example, the maximum rotation angle $\alpha_{max}$ can be can be approx. 160-180°.

The rotation results in a maximum adjustment of the distance between the second intermediate stent segment 13' and the third intermediate stent segment 13" from the minimal distance D1 (see FIG. 3) to the maximum distance D3 (see FIG. 4).

As such, the resulting overall stent length Z'" is composed of the individual stent length X1, X2 and three times X3, as well as one minimum distance D1 (between the distal stent segment 12 and the third intermediate stent segment 13"), an intermediate distance D2 as being set in FIG. 4, as well as two times the maximum distance D3 as being set in FIGS. 2 and 4.

Here it is to be noted that the second next proximal stent 13' is already inserted and deployed within the vein, with the remainder of the stents 13"-12 still accommodated in a compressed state within the catheter stent insertion device.

It will be clear that with the subsequent rotation of parts of the stent assembly 10, that is the rotation of all or less stent segments around the longitudinal stent axis 10c around any desired rotation angle between 0° (corresponding with no distance adjustment, thus the distance will remain minimal) and $\alpha_{max}$ (corresponding with the maximum distance adjustment D3) relative to the static, unmovable already deployed stent segments, the distance between each adjacent stent segment can be adjusted at any desired intermediate distance between the minimum length D1 and the maximum length D3, the latter maximum length D3 corresponding with the length of the rigid elongated filament rods 31-32.

The amount of adjustment of the individual distances between the several adjacent stent segments can be arbitrarily chosen by the physician upon placement of the stent assembly 10 within the vein, for example depending on the local constrictions within the vein. As such, the individual locations of the several stent segments, in particular the intermediate stent segments 13-13'-13" within the overall stent length, can be based on real-time imaging techniques, such as fluoroscopy, which are commonly used during stent placements.

FIGS. 5A, 5B and 5C show in more detail the length adjustment principle according to the invention. FIGS. 5A, 5B and 5C show enlarged views of the stent assembly 10 of FIGS. 1-4 in particular of the interconnection between two adjacent intermediate stent segments 13 and 13'. Intermediate stent segment 13 can be regarded as the first intermediate stent segment, whereas the intermediate stent segment 13' can be regarded as the second intermediate stent segment, seen from the proximal stent segment 11 towards the distal stent segment 12.

Both first and second intermediate stent segments 13 and 13' are interconnected with each other, using segment inter- connection means or segment interconnection elements, denoted with reference numeral 30. In an example, the segment interconnection means or elements 30 comprise—for interconnecting the two adjacent intermediate stent segments 13 and 13'—a first elongated filament rod 31 and a second elongated filament rod 32.

However, for a proper operation of the invention also one elongated filament rod 31 suffices. In another embodiment, even three elongated filament rods can be implemented as being part of the segment interconnecting means 30.

Both the first and second elongated filament rod 31 (32) are essentially rigid in their elongated orientation and can be made from the same mesh material as the material of which the intermediate stent segments 13-13'-13" as well as the proximal and distal stent segments 11 and 12 are made of. In an example, the material of the intermediate stent segments 13-13'-13" and the proximal and distal stent segments 11 and 12 as well as of the segment interconnecting means 30 (the elongated filament rod) is Nitinol. Nitinol is a body-friendly metal memory material that, due to the external compression and mechanical forces to which stents, once implanted in a vein, are subjected to, is used as the standard flexible stent material.

Each elongated filament rod 31 (32) of the segment interconnecting means or elements 30 comprise a proximal rod end 31a (32a) which is fixedly connected at connection point 13b1 (13b2) at the circumferential edge of the distal segment end 13b of the first intermediate stent segment 13. Likewise, each elongated filament rod 31 (32) comprises at the opposite end of the rod a distal rod end 31b (32b), which is likewise connected in a fixed manner at fixed locations, indicated as connection points 13a1' (13a2') at the circumferential edge of the proximal segment face 13a' of the second intermediate stent segment 13', which is positioned in a distal orientation relative to the first intermediate stent segment 13.

As it will be seen in FIG. 5A, both elongated filament rods 31 and 32 do not extend in a straight manner parallel to the longitudinal axis 10c of the stent assembly 10 (see also FIG. 1).

Instead, as clearly depicted in FIG. 5A, where the distance D1 between both intermediate stent segments 13 and 13' is minimal, both proximal and distal rod ends 31a and 31b of the first elongated filament rod 31 are radially offset with respect to each other, seen in the direction of the longitudinal stent axis 10c. The same applies to the proximal and distal rod ends 32a and 32b of the second elongated filament rod 32. Both the proximal and distal rod ends 31a-31b (32a-32b) interconnect both intermediate stent segments 13 (13') at their circumferential edge of their respective stent segment body. In the initial configuration wherein the distance D1 between both adjacent intermediate stent segments 13 and 13' is minimal (theoretically 0 (zero) mm, but in practice between 0.5-1.0 mm), the elongated filament rod 31 (32) forms an angle with the perpendicular proximal segment face 13a' and the distal segment face 13a.

According to the invention, the stent assembly 10 (see FIG. 2) is allowed to extend along its longitudinal axis 10c by rotating one of the stent segments (here stent segment 13') around the longitudinal stent axis 10c relative to the other of the two stent segments, here the first intermediate stent segment 13.

This rotating principle is shown in FIGS. 5B and 5C by means of the black curved arrow depicted on the circumferential surface of the second intermediate stent segment 13'. By rotating the second intermediate stent segment 13' relative to the first intermediate stent segment 13, both connection points 13a1' and 13a2', where the distal rod ends 31b (32b) of both elongated filament rods 31 and 32 are connected with the proximal segment face 13a' of the second intermediate stent segment 13', rotate in a similar fashion around the longitudinal stent axis 10c, whilst the second intermediate stent segment 13' translates along the longitudinal stent axis 10c in a distal orientation relative to the first intermediate stent segment 13, which remains static and which does not displace, as depicted by the large white arrow pointing to the left in FIGS. 5B and 5C).

FIG. 5B depicts an intermediate configuration of the stent assembly 10, wherein—seen from the starting configuration depicted in FIG. 5A—the second intermediate stent segment 13' has been rotated around approx. 60-80°. Due to the rotation of the second intermediate stent segment 13' around the longitudinal stent axis 10c in the direction of the black curved arrow depicted on the circumferential surface of the second intermediate stent segment 13', both connection points 13a1' and 13a2' on the proximal segment face 13a' of the second intermediate stent segment 13' rotate likewise around the stent axis 10c.

Due to the rigid construction of the elongated filament rods 31 and 32, the distance between both proximal rod end 31a (32a) and distal rod end 31b (32b) remains constant and as such a rotation of the second intermediate stent segment 13' around the longitudinal stent axis 10c relative to the first intermediate stent segment 13 (which in this example remains static/does not displace) results in an adjustment and more in particular in an increase of the distance between both intermediate stent segments 13 and 13'.

In FIG. 5B, which depicts an intermediate configuration of the two adjacent intermediate stent segments 13 and 13', the distance between both intermediate stent segments 13 and 13', denoted with D2, is larger than the initial minimum distance as denoted with reference numeral D1 in FIG. 5A.

Further rotation of the second intermediate stent segment 13' around the longitudinal stent axis 10c relative to the proximal first intermediate stent segment 13 results in a further increase of the distance between both intermediate stent segments 13 and 13' until the maximum distance is reached. This configuration is depicted in FIG. 5C, wherein the distance between both intermediate stent segments 13 and 13' has reached its maximum length and is denoted with the reference numeral D3.

It is clear that the maximum distance D3 between both intermediate stent segments 13 and 13' depends on the length of the elongated filament rods 31 and 32, which interconnect both intermediate stent segments 13 and 13'. In FIG. 5C, depicting the maximum extension, both elongated filament rods 31 and 32 extend in a parallel orientation relative to the longitudinal stent axis 10c.

Please note that in a mechanical equivalent configuration, the first, proximal intermediate stent segment 13 can be rotated around the stent axis 10c and thus advanced in the proximal direction along the stent axis 10c with the proximal stent segment 11, relative to the second, intermediate stent segment 13', which remains static and which does not displace (in either rotational and longitudinal direction relative to the stent axis 10c).

Thus it is to be noted that the stent elongated principle as depicted in FIGS. 1-5 is meant as an example and is not to be considered the only possibility to lengthen a stent assembly according to the invention, that is consisting of five stent segments. Any distance between either adjacent stent segments can be altered and elongated to any distance between its minimal (D1) and maximal value (D3). D1 theoretically equals 0 (zero) mm, but in practice the minimal value of D1 is approx. 0.5-1.0 mm. Similarly one or more distances between adjacent stent segments can remain unaltered (stay at their minimal length D1), in fact they can be skipped, whereas a specific distance is to be changed, upon decision by the physician, who decides on the ultimate stent lengthening based on the local restrictions within the vein near the intended deployment position of the stent assembly 10.

With the stent elongation mechanism as described in this patent application, the physician can easily adapt the stent length and in particular set the location of a specific intermediate stent segment within the overall stent assembly, such that each intermediate stent segment abuts and supports several desired locations of the vessel wall of the vein after insertion and deployment.

As stated above in an example of the deployment technique each next proximal stent is already inserted and deployed within the vein, with the remainder of the stents still accommodated in a compressed state within the catheter stent insertion device and arranged for a next length adjustment. Once the physician is of the opinion that the overall stent assembly 10 has the correct length and the correct initial proximal position within the vein, the decision is made to insert and deploy the remainder of the stent segments within the vein under simultaneous withdrawal in the distal direction of the catheter stent insertion device. As such the complete stent assembly 10 with the correct, adjusted length will be deployed within the vein covering the correct vessel length as intended.

In another example of the deployment technique the complete stent assembly 10 is adjusted to its correct overall length by adjusting each separate distance between adjacent stent segments. Once the physician is of the opinion that the overall stent assembly 10 has the correct length and the correct initial proximal position within the catheter stent insertion device, the decision is made to insert and deploy the complete stent assembly with all stent segments in one insertion/deployment step within the vein under simultaneous withdrawal in the distal direction of the catheter stent insertion device. As such the complete stent assembly 10 with the correct, adjusted length will be deployed within the vein covering the correct vessel length as intended.

Figure 6:
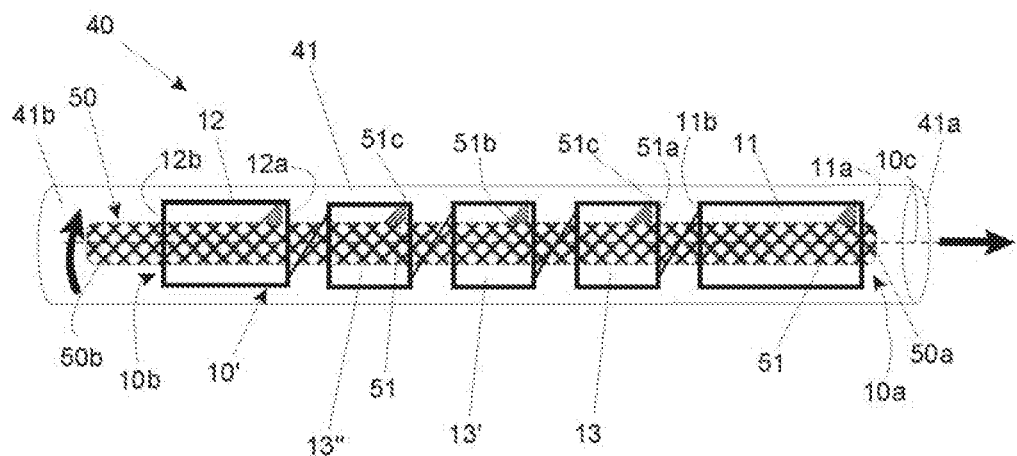
FIG. 6 a schematic example of a catheter stent insertion device according to the invention.

In FIG. 6 a catheter stent insertion device 40 according to the invention is disclosed. The catheter stent insertion device 40 is schematically depicted and is composed of a hollow stent accommodating tube 41 for accommodating the stent (also indicated as the stent assembly) 10 in a compressed configuration. The hollow stent accommodating tube 41 has a proximal tube end 41a (depicted at the right side of the page of FIG. 6) which is open, as well as a distal tube end 41b (depicted at the left side of the page of FIG. 6). The distal tube end 41b is connected to guidance means (not depicted) which are positioned outside the human body.

The catheter stent insertion device 40 is to be inserted with its proximal tube end 41a inside the vein towards the intended deployment location. At said location the stent (assembly) 10 is to be deployed, such that after deployment within the vein the separate stent segments expand and abut against the inner vessel wall of the vein.

The catheter stent insertion device 40 also comprises deployment means depicted with reference numeral 50, which are, in this example, constructed as a deployment spindle 50. The deployment spindle 50 is in essence rigid, but for example can also be made as a flexible wire, in particular made from a plastic. The deployment spindle or deployment wire 50 is accommodated inside the hollow stent accommodating tube 41 and more particularly is also accommodated inside the hollow cylindrically configured yet compressed stent 10.

It is to be noted that FIG. 6 depicts the catheter stent insertion device 40 in an enlarged view and it should be clarified that the dimensions of the several parts are such that the stent assembly 10 in its compressed configuration is closely placed around the deployment spindle 50 and is also closely encapsulated within the hollow stent accommodating tube 41. As such the miniaturized configuration allows the insertion inside a vein of a human or an animal body.

The deployment spindle 50 is provided with several stent segment engagement notches 51. Each stent segment engagement notch 51 engages an individual stent segment 11-13-13'-13"-12 near each proximal stent face 11a (13a, 12a). As each stent segment is manufactured of a metal mesh material, such as Nitinol, each stent segment engagement notch 51 exhibits a radially outward projection 51c, which engages the mesh material of the respective stent segment and more in particular slightly protrudes out of the circumferential surface of the respective stent segment.

The protruding notch tip 51c ensures that during advancement of the deployment spindle 50 in the direction of the open proximal tube end 41a (depicted with the bold arrow pointing to the right in FIG. 6), each pointed notch tip 51c engages the metal mesh material of the individual stent segment. As such a longitudinal advancement of the deployment spindle 50 in the direction of the open proximal tube end 41a results in an similar advancement of the whole stent assembly 10. This means that all stent segments of the stent assembly 10 within the hollow stent accommodating tube 41 advance towards the open tube end 41a. Ultimately the advancement will result in a deployed within the vein at the desired or intended deployment location, after which the stent assembly deploys and expands and abuts against the inner vessel wall of the vein.

In a similar fashion as disclosed and described with reference to FIGS. 1-5 the deployment spindle 50 is rotatable about the longitudinal axis 10c and as such the notch tip 51c also engages the metal mesh material of the respective stent segment in a rotational direction. The rotation of the deployment spindle 50, whilst engaging one or more of the stent segments of the stent assembly 10, results in an adjustment of the distance between the relevant adjacent stent segments between a first configuration wherein the distance is minimal and a second configuration wherein the distance is maximal and in relation to the next proximal stent segment, which does not rotate but remains static and in place within the hollow stent accommodating tube 41.

The amount (or angle) of rotation of the deployment spindle 50 around the longitudinal axis 10c allows for a proper adjustment of the distance between the adjacent stent segments at any distance value (in mm) between the minimal distance (D1 in the FIGS. 2-5) and the maximal distance D3 (see FIGS. 2-5) depending on the amount of rotation of the deployment spindle 50 around the axis 10c between a minimum rotation angle and a maximum rotation angle $\alpha_{max}$.

In an example the deployment spindle 50 can be rotated such that the distance between the relevant stent segments can be set at any arbitrary distance value between the minimum (D1) and maximum distance (D3).

In another example the deployment spindle 50 can only be rotated in a discrete, stepwise manner. Thus—starting from the first, initial configuration as shown in FIG. 1—the deployment spindle 50 can be rotated one step (one increment) resulting in a rotational displacement of the relevant stent segment (or stent segments as in FIG. 3, 4 or 5) about a certain angle ($\alpha_{middle}$ as shown in FIG. 4), resulting in a longitudinal displacement and subsequent elongation of the distance between the relevant stent segments from D1 (initial distance) to D2 (intermediate distance).

Figure 5:
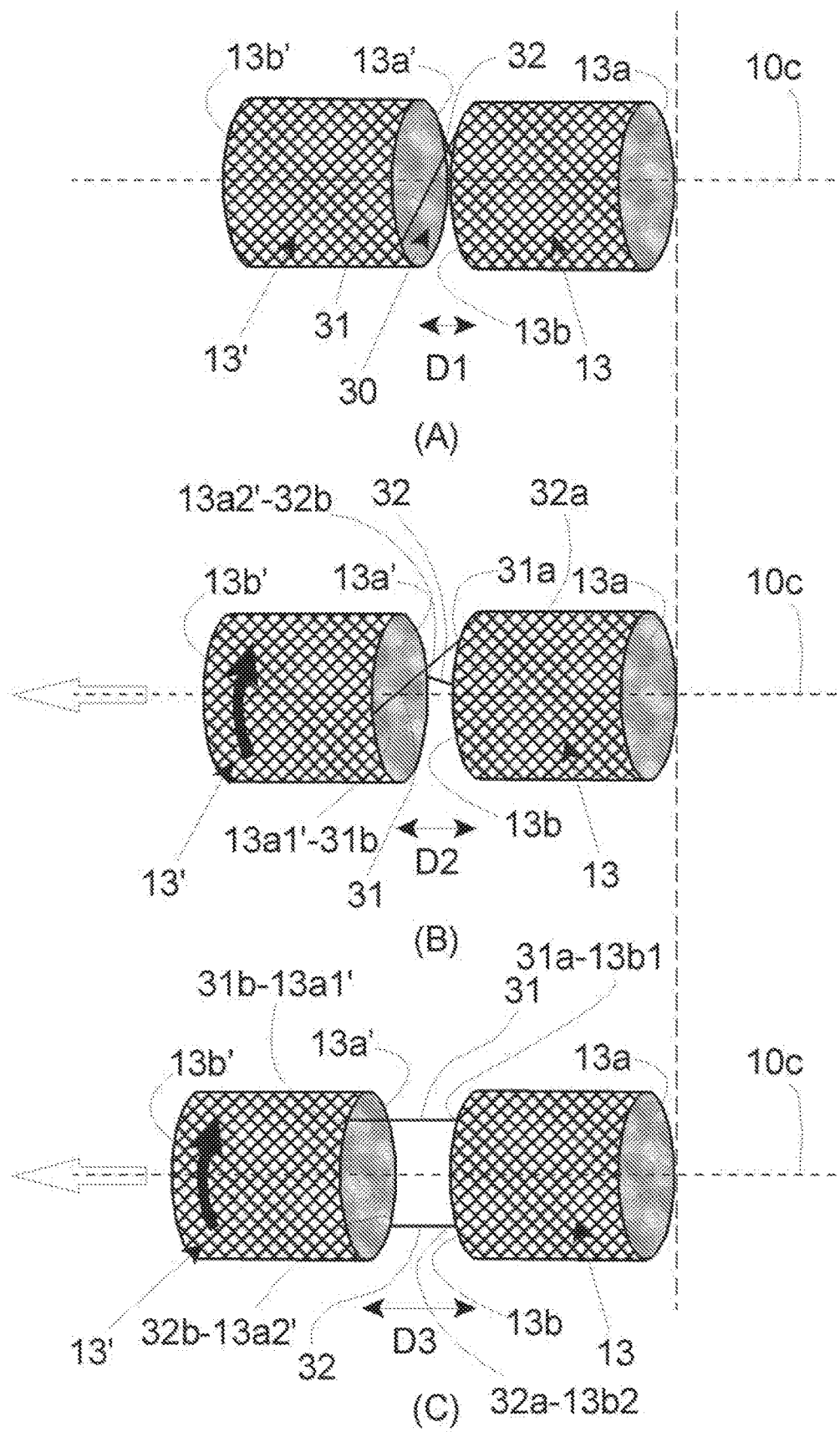

Similarly, a further incremental rotation of the deployment spindle 50 will result in a further elongation of the distance between the relevant stent segments from D2 (intermediate distance) to D3 (maximum distance). In other words, to set the distance between the relevant stent segments from its initial value D1 to its maximum value D3 requires—in this example as depicted in connection with FIGS. 1-5—requires two rotational increments of the deployment spindle 50 about a maximal angle ($\alpha_{max}$ as shown in FIGS. 3 and 5).

It will be clear that the discrete incremental rotation of the deployment spindle 50 can be configured depending on the stenting application (procedure) to be implemented. A catheter stent insertion device can be used, wherein the deployment spindle 50 is allowed a two-step incremental rotation as depicted in FIGS. 1-5, thus from the initial angle (corresponding to the minimal distance D1), towards the second first ($\alpha_{middle}$ corresponds with intermediate distance D2), and finally the second increment ($\alpha_{max}$ corresponds with maximal distance D3). In other examples deployment spindles capable of being set (rotated) at three or four or even more increments can be envisaged, allowing the distance between the relevant stent segments to be set from the initial, minimal distance D1 towards intermediate distances D2'-D3'-D4 (in the event of three increments, with D4 representing the maximal distance).

In the two-increment example $\alpha_{middle}$ can correspond to a rotation of the deployment spindle 50 over 70-90°, whereas $\alpha_{max}$ can correspond to a maximum rotation of the deployment spindle 50 over 140-180°.

In an example of a three-increment example the respective two incremental rotation angles $\alpha_{increment}$ can correspond to a rotation of the deployment spindle 50 over 60°-120°, each whereas the final, third increment $\alpha_{max}$ still can correspond to a maximum rotation of the deployment spindle 50 over approx. 170°-180°.

In an example of a four-increment example the respective three incremental rotation angles $\alpha_{increment}$ can correspond to a rotation of the deployment spindle 50 over 45°-90°-135°, each whereas the final, fourth increment $\alpha_{max}$ still can correspond to a maximum rotation of the deployment spindle 50 over approx. 170°-180°.

In either incremental implementation of the catheter stent insertion device according to the invention the distance adjustment between two adjacent stent segments can be adjusted in a stepwise manner between the minimum distance D1 and the maximum distance D3, which maximum distance may correspond with 5-20 mm. Each incremental adjustment can result in a distance adjustment of 1-5 mm depending on the number of allowed/possible increments.

The longitudinal and rotational manipulation of the deployment spindle 50 can be performed by means of the guidance means, which also advance the catheter stent insertion device through the vein towards the intended deployment location, or by hand by the physician. In either method (automated or by hand) the location of the (proximal device end 41a of the) catheter stent insertion device prior to deployment of the stent 10 can be checked under fluoroscopy or with any other known imaging technique being used with stent placement.

The proximal contact phase 51a of the stent segment engagement notch 51 is oriented towards the proximal tube end 40*a* and set proximal contact surface exhibits an acute angle with respect to the longitudinal axis 10*c* seen in the direction of the open proximal tube end 41*a*. Said acute angle of the proximal contact surface with the longitudinal axis 10*c* is 90° or less. The stent segment engagement notch 51 also exhibits a contact surface 51*b* which is oriented towards the distal tube end 40*b* which distal contact surface 51*b* exhibits an obtuse angle with the longitudinal axis seen in the direction towards the distal tube end 40*b*. Said obtuse angle is in an example between 120°-150° degrees. The obtuse angle of the distal contact surface 51*b* allows a proper withdrawal of the deployment spindle 50 in a distal direction without engaging the metal mesh material of the several stent segments. In fact due to the obtuse angle the metal mesh material of the stent segments will slip over and off from the stent segment engagement notch and thus prevents an undesired hooking of said metal mesh material with the stent segment engagement notch.

As with the catheter stent insertion device 40 of FIG. 6 each individual next proximal stent segment can be inserted and deployed one by one within the vein by a longitudinal displacement of the deployment spindle 50 towards the proximal device end 41*a*. After deployment of one of the stent segments, the remainder of the stents still accommodated in a compressed state within the hollow stent accommodating tube 41 of the catheter stent insertion device can be subjected to a next length adjustment by the subsequent rotation of the deployment spindle 50 over the desired angle or increments. After the subsequent length adjustment each next proximal stent segment within the hollow stent accommodating tube 41 can be deployed within the vein using the deployment spindle 50 until all stent segments are inserted and deployed covering the correct vessel length as intended.

REFERENCE NUMERAL LISTING

10 stent
10*a* proximal stent end of stent 10
10*b* distal stent end of stent 10
10*c* longitudinal axis of stent 10
11 first, proximal stent segment
11*a* proximal end of proximal stent segment
11*b* distal end of proximal stent segment
12 second, distal stent segment
12*a* proximal end of distal stent segment
12*b* distal end of distal stent segment
13 first intermediate stent segment
13*a* proximal end of intermediate stent segment
13*b* distal end of intermediate stent segment
13*b*1 first connection between distal end of first intermediate stent segment and proximal rod end 31*a* of first elongated filament rod 31
13*b*2 second connection between distal end of first intermediate stent segment and proximal rod end 32*a* of second elongated filament rod 32
13' second intermediate stent segment
13*a*1' first connection between proximal end of further intermediate stent segment 13' and distal rod end 31*b* of first elongated filament rod 31
13*a*2' second connection between proximal end of further intermediate stent segment and distal rod end 32*b* of second elongated filament rod 32
13" third intermediate stent segment
30 segment interconnecting means
31 first elongated filament rod
31*a* proximal rod end of first elongated filament rod
31*b* distal rod end of first elongated filament rod
32 second elongated filament rod
32*a* proximal rod end of second elongated filament rod
32*b* distal rod end of second elongated filament rod
D1 initial, minimal distance between two intermediate stent segments
D2 intermediate distance between two intermediate stent segments
D3 maximum distance between two intermediate stent segments
X1 length of first, proximal stent segment 11
X2 length of second, distal stent segment 12
X3 length of intermediate stent segment 13-13'-13"
Z initial length of the stent of FIG. 1
Z' an intermediate length of the stent of FIG. 2
Z" a further intermediate length of the stent of FIG. 3
Z''' a further intermediate length of the stent of FIG. 4
40 catheter stent insertion device
41 hollow stent accommodating tube
41*a* open proximal tube end
41*b* distal tube end
50 deployment means or deployment spindle
50*a* proximal spindle end
50*b* distal spindle end
51 stent segment engagement notch
51*a* proximal contact face
51*b* distal contact face
51*c* notch tip

The invention claimed is:

1. A stent for insertion in a vein of a human or animal body, said stent having a proximal end, a distal end and a longitudinal stent axis, and comprising at least two stent segments, as well as segment interconnecting means interconnecting two stent segments, wherein said segment interconnecting means are arranged in adjusting a distance between said two stent segments between a first configuration, wherein said distance is minimal and a second configuration, wherein said distance is maximal, due to a rotation around said longitudinal stent axis of one of said two stent segments relative to the other of the two stent segments, wherein, for interconnecting said at least two stent segments, said segment interconnecting means comprise at least one elongated filament rod having two rod ends, a first rod end being connected to the first stent segment and the second rod end being connected to the second stent segment, wherein in said first configuration said first rod end and said second rod end are radially offset with respect to each other and wherein in said second configuration said first rod end and said second rod end are longitudinally aligned with respect to each other.

2. A stent for insertion in a vein of a human or animal body according to claim 1, wherein said stent comprises a proximal stent segment, a distal stent segment and one or more intermediate stent segments disposed between the proximal and distal stent segments, and wherein said segment interconnecting means interconnect each of said stent segments.

3. A stent for insertion in a vein of a human or animal body according to claim 2, wherein, seen along said longitudinal axis of the stent, said proximal stent segment has a first length, said distal stent segment has a second length, and said intermediate stent segments have a third length, wherein said third length is smaller than said first and second lengths.

4. A stent for insertion in a vein of a human or animal body according to claim 3, wherein said third length is 5-15 mm.

5. A stent for insertion in a vein of a human or animal body according to claim 3, wherein said first length and said second length are the same.

6. A stent for insertion in a vein of a human or animal body according to claim 3, wherein said first length is longer than said second length, and wherein said first length is 30-50 mm and said second length is 10-30 mm.

7. A stent for insertion in a vein of a human or animal body according to claim 2, wherein the number of said intermediate stent segments is between 1-30 segments.

8. A stent for insertion in a vein of a human or animal body according to claim 1, wherein said maximal distance between said stent segments is between 5-20 mm.

* * * * *